US00PP13521P2

(12) United States Plant Patent
Lemon

(10) Patent No.: US PP13,521 P2
(45) Date of Patent: Jan. 28, 2003

(54) GERANIUM PLANT NAMED 'STARDOM PINK AND WHITE'

(75) Inventor: David Lemon, County of Santa Barbara, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/877,264

(22) Filed: Jun. 8, 2001

(51) Int. Cl.[7] ..... A01H 5/00
(52) U.S. Cl. ..... Plt./324
(58) Field of Search ..... Plt./324

*Primary Examiner*—Bruce R. Campell
*Assistant Examiner*—Annette Para
(74) *Attorney, Agent, or Firm*—Webb Ziesenheim Logsdon Orkin & Hanson, P.C.

(57) ABSTRACT

A new and distinct floribunda geranium plant with pink and white colored semi-double flowers above medium green foliage.

1 Drawing Sheet

CLASSIFICATION

*Pelargonium×hortorum.*

VARIETAL DENOMINATION

'Stardom Pink and White'.

BACKGROUND OF THE INVENTION

The present invention comprises a new and distinct cultivar of *Pelargonium×hortorum* known by the varietal name 'Stardom Pink and White', Breeder No. 6DG2570. The new variety was discovered in Lompoc, Calif. The new variety is a result of cross breeding of Seedling Single White #2077 (female) (unpatented) and 'Maureen' (male) (U.S. Plant Pat. No. 10,512). The new variety exhibits similar flower color to 'Maureen', but differs in its double flowers compared to the female parent's single flowers and different flower color than 'Maureen'. The flower color of the new variety is deeper than that of 'Eclipse Light Salmon' (U.S. Plant Pat. No. 7,926. The new variety was first asexually reproduced by cuttings in Lompoc, Calif. The new variety has been trial and field tested and has been found to retain its distinctive characteristics and remain true to type through successive propagations.

The new variety, when grown in a glass greenhouse in Connellsville, Pa. using full light, 60° F. night temperature and 68° F. day temperature and grown in a soilless media with constant fertilizer at 200–250 ppm nitrogen and potassium has a response time of six weeks to flowering from a rooted cutting to flowering in a 10 cm pot.

DESCRIPTION OF THE DRAWING

The accompanying photographic drawing illustrates the new variety, with the color being as nearly true as it is possible with color illustrations of this type.

DESCRIPTION OF THE PLANT

The following detailed description sets forth the characteristics of the new cultivar at 12 weeks grown from a rooted cutting. The data which defines these characteristics were collected by asexual reproductions carried out at Oglevee, Ltd. in Connellsville, Pa. The color readings on a plant in an 8 inch cm pot were taken on Jan. 4, 2001 indoors under 200–220 foot candles of cool white fluorescent light. Color references are primarily to the R.H.S. Colour Chart of The Royal Horticultural Society of London.

PLANT

Form: Uniform mound.
Height: 17–22 cm from top of media surface.
Growth: Self-branching with some cascading growth.
Strength: Free standing; does not require artificial support.
Foliage: Stalked leaf attachment.
Rooting time: 14–21 days to visible root.
Leaves:
- *Size.*—4.0–5.0 cm long at longest point; 6.5–9.5 cm wide at widest point.
- *Shape.*—Reniform; cordate base.
- *Margin.*—Crenate.
- *Texture.*—Pubescent, smooth.
- *Color.*—Upper surface: Green Group 137A. Lower surface: Green Group 137C.
- *Ribs and veins.*—Type: Palmate. Color: Yellow-Green Group 145C.

Petioles:
- *Color.*—Yellow-Green Group 144C.
- *Length.*—8.0–11.0 cm.

Stem:
- *Color.*—Yellow-Green Group 144C.
- *Internode length.*—0.6–1.0 cm.

THE BUD

Shape when just showing color:
- *Overall.*—Flat, semi-circular.
- *Individual bud.*—Round.

Size when just showing color:
- *Size of cluster.*—2.3–2.6 cm wide.
- *Individual bud.*—0.5–0.8 cm wide; 0.6–0.8 cm long.
- *Number of buds per cluster.*—6–10.

INFLORESCENCE

Size of umbel: 5.5–8.5 cm.
Borne: Flowers on pedicel; pedicel on peduncle; 0.5–10.0 cm above foliage.
Number of flowers per umbel: 4–10.

Flowers:

*Form.*—Slightly cupped, petals overlap and are slightly ruffled on edges lending a very ruffled effect.

*Size.*—3.5–4.3 cm wide; 1.0–1.5 cm deep.

*Petals.*—Shape: Obovate. Size: 1.8–2.2 cm long; 1.3–2.0 cm wide. Margin: Entire. Number per flower: 13–17. Color: Upper surface: Petals are pink with white at base "blushing" out toward the outer edge in almost an "air brush effect" pattern. Varying degrees of white are present depending on the individual petal. On some, the white tends to streak out in an almost line formation, while on others it is a full area of white with tiny little dots of white blushing into the pink. Pink shades at the outer edge of the flowers range from at darkest Red-Purple Group 68A, Red-Purple Group 67C, and Red Group 55A, to the lighter shades of Red Group 55B and Red-Purple Group 62B. Toward the middle of the petal where the white meets the pink, the pink shades include not only the colors mentioned above in very tiny specks (yielding a lighter effect) but also Red-Purple Group 68D, and Red-Purple Group 67D. As the flower ages, the overall flower color fades and the white become more pronounced. Pink shades on older flowers are Red-Purple Group 62A, Red-Purple Group 58D, Red-Purple Group 68A, and Red Group 55B. Once again the light colors toward the center of the petal are mostly achieved by the same colors in the outer edge of the petal in very small dots or specks separated by areas of white. Lower surface: White at petal base moves into pink toward the outer edge in gradient shades of pink, Red-Purple Group 62C, Red Groups 55C and 55D, and lighter Red Groups 56B and 56C. Older petals tend to be lighter, mimicking the lighter shades found on the younger petals.

*Texture.*—Smooth, slightly reflective.

*Tonality from a distance.*—A dramatic show of pinks including bright clear watermelon pinks, bluer candy pinks, and some purple-pink shades at outer edges of flower fading to a white toward the center of this ruffled, semi-double flower.

Petaloids:

*Number.*—0–2.

*Shape.*—Irregular; can be petal shaped but twisted, but most observed were tubular.

*Color.*—Same as petals with varying degrees of pinks with white.

Pedicel:

*Length.*—2.3–2.7 cm.

*Color.*—Yellow-Green Group 144B.

Peduncle:

*Length.*—12.9–14.5 cm.

*Color.*—Yellow-Green Group 144B.

Disease/pest resistance: No unusual susceptibility to diseases or pests has been noted to date.

Lasting quality: Umbels will last 7–14 days.

Fragrance: None.

REPRODUCTIVE ORGANS

Stamens:

*Quantity.*—2–5, often attached to petaloids.

*Anthers.*—0.1–0.15 cm.

*Filaments.*—Length: 0.5–0.8 cm. Color: White.

*Pollen color.*—Orange.

Pistils:

*Number.*—One.

*Length.*—0.6–0.8 cm.

*Stigma.*—Number: One. Color: White.

*Style.*—Length: 0.1–0.3 cm. Color: White.

Ovaries:

*Color.*—Green.

*Length.*—0.4–0.6 cm.

*Width.*—0.2–0.25 cm.

*Pubescence.*—Pubescent.

*Completeness.*—Superior.

Fruit: None observed.

I claim:

1. A new and distinct variety of floribunda geranium plant substantially as shown and described.

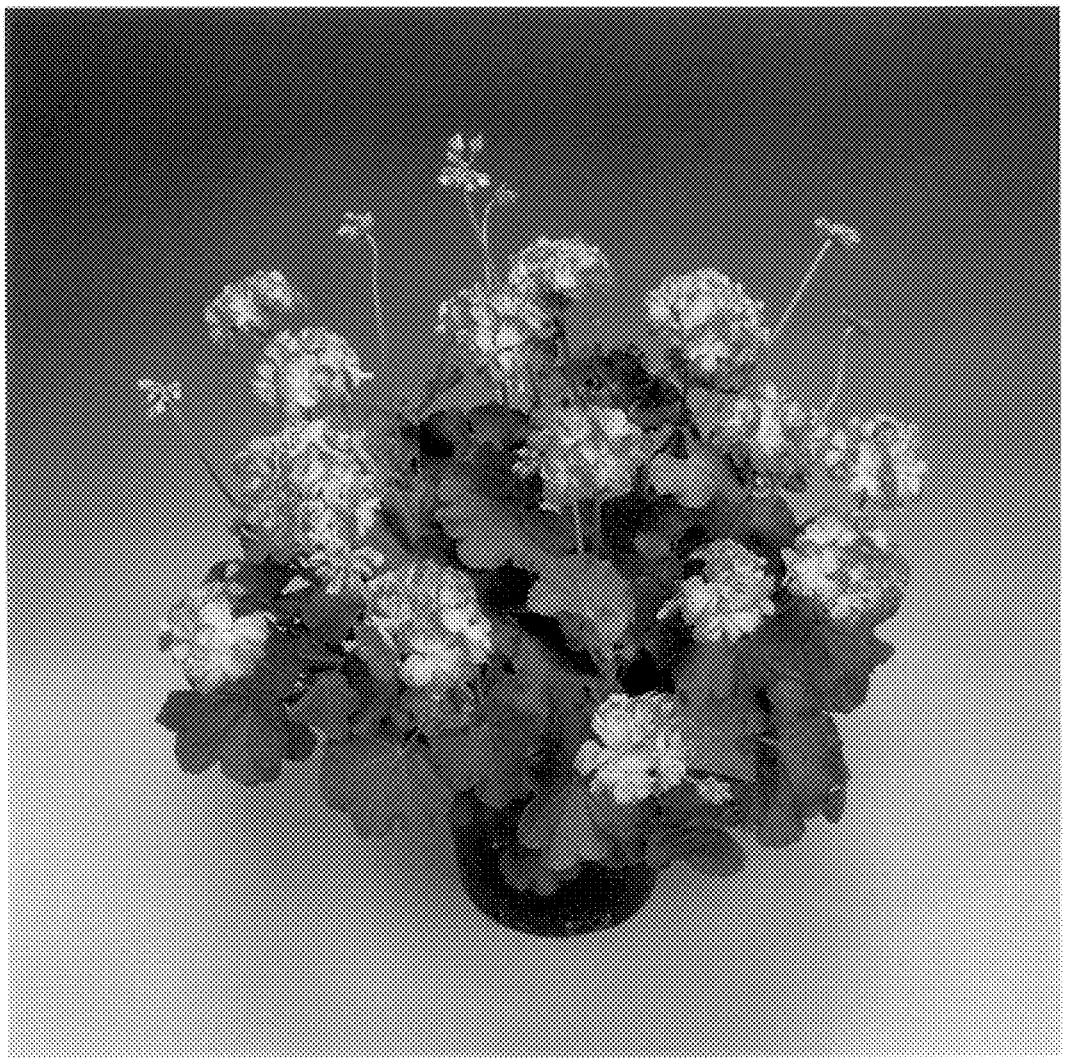

* * * * *